(12) United States Patent
Puchek

(10) Patent No.: US 7,563,224 B2
(45) Date of Patent: Jul. 21, 2009

(54) METHOD OF TREATING A SEVERE DIABETIC ULCER

(75) Inventor: Daniel R. Puchek, Scottsdale, AZ (US)

(73) Assignee: ProMedTek, Inc., Scottsdale, AZ (US)

( * ) Notice: Subject to any disclaimer, the term of this patent is extended or adjusted under 35 U.S.C. 154(b) by 0 days.

(21) Appl. No.: 11/943,522

(22) Filed: Nov. 20, 2007

(65) Prior Publication Data

US 2008/0125617 A1    May 29, 2008

Related U.S. Application Data

(60) Provisional application No. 60/860,127, filed on Nov. 20, 2006, provisional application No. 60/860,126, filed on Nov. 20, 2006, provisional application No. 60/860,115, filed on Nov. 20, 2006.

(51) Int. Cl.
*A61N 1/00* (2006.01)
(52) U.S. Cl. .......................................... 600/14; 600/15
(58) Field of Classification Search .............. 600/9–15; 607/50–52, 144–145, 149; 128/897–898
See application file for complete search history.

(56) References Cited

U.S. PATENT DOCUMENTS

| | | | |
|---|---|---|---|
| 4,937,323 A | 6/1990 | Silver et al. .................. 530/356 |
| 5,514,079 A | 5/1996 | Dillon .......................... 601/151 |
| 6,132,362 A | 10/2000 | Tepper et al. .................. 600/14 |
| 6,155,966 A | 12/2000 | Parker ........................... 600/13 |
| 6,334,069 B1 | 12/2001 | George et al. .................. 607/2 |
| 6,353,763 B1 | 3/2002 | George et al. ................. 607/50 |
| 6,420,594 B1 | 7/2002 | Farone et al. ................ 560/185 |
| 6,639,098 B2 | 10/2003 | Farone et al. ................ 560/189 |
| 6,745,078 B1 * | 6/2004 | Buchner ....................... 607/72 |
| 6,846,480 B2 | 1/2005 | Smith et al. ................. 424/70.1 |
| 6,846,947 B2 | 1/2005 | Farone et al. ................ 560/147 |
| 6,956,144 B2 | 10/2005 | Molan .......................... 602/48 |
| 6,967,281 B2 | 11/2005 | George et al. ................ 174/368 |
| 6,974,961 B1 | 12/2005 | George et al. ............. 250/516.1 |

(Continued)

OTHER PUBLICATIONS

Armstrong et al., "Evidence-Based Orthopaedics: Intermittent Pneumatic Compression Promoted Healing in Foot Infections", *The Journal of Bone and Joint Surgery*, 83(5):787 (2001).

(Continued)

*Primary Examiner*—John P Lacyk
(74) *Attorney, Agent, or Firm*—Fennemore Craig, P.C.

(57) ABSTRACT

The present invention is directed to a specialized method of treating a severe diabetic ulcer that penetrates the subcutaneous fat layer of a patient. The method comprises the steps of: administering a treatment session to a diabetic patient having a severe diabetic ulcer, the treatment session comprising at least three pulsed electromagnetic fields (PEMF) applications, PEMF applications 1, 2, and 3, and at least two intermittent compression therapy (ICT) applications. The PEMF application and ICT therapy settings address specific factors that are necessary to induce healing of the diabetic ulcer and prevent amputation. In a preferred embodiment, the treatment session further comprises the step of applying a dressing having a silver and/or honey anti-infection composition thereon to the ulcer area to impede microbial growth in the ulcer area. In another embodiment, the method includes the step of applying ultrasound to the ulcer area for a time sufficient to inhibit microbial growth.

25 Claims, 1 Drawing Sheet

U.S. PATENT DOCUMENTS

| | | | |
|---|---|---|---|
| 7,024,239 B2 | 4/2006 | George et al. | 607/2 |
| 7,135,195 B2 | 11/2006 | Holladay et al. | 424/618 |
| 2002/0169356 A1 | 11/2002 | Ross | 600/14 |
| 2006/0129189 A1 | 6/2006 | George et al. | 607/2 |
| 2006/0142198 A1 | 6/2006 | Gandy | 514/12 |
| 2006/0149171 A1 | 7/2006 | Vogel et al. | 601/11 |
| 2006/0212077 A1* | 9/2006 | Pilla et al. | 607/2 |
| 2006/0235350 A1 | 10/2006 | Alimi et al. | 604/19 |

OTHER PUBLICATIONS

Gilbert et al., "The Provant® Wound Closure System Induces Activation of p44/42 MAP Kinase in Normal Cultured Human Fibroblasts", *Ann. N.Y. Acad. Sci.*, 961:168-171 (2002).

International Search Report for PCT/US2007/085310 dated Jul. 1, 2008 (2 sheets).

Kavros et al., "Improving Limb Salvage with Intermittent pneumatic Compression in Patients with Critical Limb Ischemia: The Mayo Clinic Experience", (1998-2004).

Mayrovitz, Harvey N., "Electromagnetic Linkages in Soft Tissue Wound Healing", *Bioelectromagnetic Medicine*, 30:461-483 (2004).

Montori et al., "Intermittent compression pump for nonhealing wounds in patients with limb ischemia", *International Angiology*, 21(4):360 (Dec. 2002).

Nikolovska et al., "Evaluation of two different intermittent pneumatic compression cycle settings in the healing of venous ulcers: A randomized trial", *Med Sci Monit.*, 11(7):CR337-343 (2005).

Ritz et al., "Provant® Wound-Closure System Accelerates Closure of Pressure Wounds in a Randomized, Double-Blind, Placebo-Controlled Trial", *Ann. N.Y. Acad. Sci.*, 961:356-359 (2002).

Stiller et al., "A portable pulsed electromagnetic field (PEMF) device to enhance healing of recalcitrant venous ulcers: a double-blind, placebo-controlled clinical trial", *British Journal of Dermatology*, 127:147-154 (1992).

Written Opinion of the International Searching Authority for PCT/US2007/085310 dated Jul. 1, 2008 (7 sheets).

* cited by examiner

METHOD OF TREATING A SEVERE DIABETIC ULCER

RELATED APPLICATION DATA

This application is based on and claims the benefit of U.S. Provisional Patent Application Nos. 60/860,127, 60/860,126 and 60/860,115, all filed on Nov. 20, 2006, the disclosure of each of which is incorporated hereby by this reference.

FIELD OF THE INVENTION

The present invention is directed to a method for treating a patient having ischemia and a severe diabetic ulcer that penetrates the subcutaneous fat layer.

BACKGROUND OF THE INVENTION

Severe diabetic ulcers are often a complication of diabetes and are characterized as having a wound that penetrates the subcutaneous fat layer and ischemia. Approximately 18 million people in the U.S have diabetes and over 800,000 new cases are diagnosed each year. A significant percentage of those with diabetes, about 2.7 million, develop ulcers, e.g. foot ulcer. Of those with ulcers, about 1.2 million will develop a severe diabetic ulcer. Severe diabetic ulcers too often lead to infection, gangrene, amputation, and sometimes morbidity. In fact, diabetes is the most common underlying cause of lower extremity amputation in the United States and Europe.

Severe diabetic ulcers are difficult to treat as is evidenced by the high percentage of ulcers that result in amputation. Severe diabetic ulcers are extremely complex to treat having multiple, overlapping complications that impede or completely inhibit the patients healing process, e.g., ischemia, open and deep wound, infection, etc. The therapies presently on the market are typically designed for all types of wounds and do not adequately address the problematic issues of complex wounds, such as severe diabetic ulcers.

As evidenced above, a need exist for an improved method for treating severe diabetic ulcers specifically to reduce and/or prevent amputation. The present invention addresses this need and provides a method of successfully treating severe diabetic ulcers to induce healing and to prevent multiple amputations of the extremities of the diabetic patient.

SUMMARY OF THE INVENTION

The present invention is directed to a method specifically designed to treat severe diabetic ulcers. The present method preferably comprises the steps of: administering to a diabetic patient, suffering from a severe diabetic ulcer and ischemia a treatment session comprising at least three pulsed electromagnetic field (PEMF) applications, PEMF applications 1, 2, and 3, and at least two intermittent compression therapy (ICT) applications. Preferably the treatment session is applied to the diabetic patient at least once a day to treat the severe diabetic ulcer, more preferably at least twice a day. The typical treatment session is at least about 2.5 to 3.5 hours. Preferably, the treatment session is administered at least once a day, more preferably at least twice a day, and most preferably every 7 to 10 hours after completion of the previous treatment session.

The method developed by the inventor is a specialized treatment that addresses the unique and problematic characteristics of severe diabetic ulcers. The specific PEMF application combination and settings address specific factors that are necessary to induce healing of severe diabetic ulcers. For example, PEMF application 1 is designed to induce cell activity necessary to prepare the ulcer bed for healing; PEMF application 2 induces cell activity necessary to fill in the ulcer bed near the surface of the patient's skin during the healing process or for shallower diabetic ulcers; PEMF application 3 is designed to induce cell activity to fill in the ulcer bed further from the surface. PEMF application 3 is especially important for deep problematic diabetic ulcers. An optional PEMF application 4 is designed to induce cell activity to fill in the wound bed for problematic diabetic ulcers that are not fully responsive to PEMF application 2 and/or 3.

The present invention allows for multiple settings to deliver specific types of both PEMF and ICT therapies during the treatment sessions. The ICT therapy administered to the patient is chosen based on the level of ischemia and level of patient sensitivity. The ICT therapy preferably has at least two settings, a venous and arterial setting. The venous setting is used to address the patient's venous insufficiencies and the arterial setting is used to address the patient's arterial insufficiencies. In a preferred embodiment, a third optional ICT therapy setting, venous/arterial therapy, is used to address both the patient's venous and arterial insufficiencies in the ulcer area together at one time. In a preferred embodiment, the ICT therapies of the present invention are specifically designed to address the patient's vascular needs, having specific cycle of inflation time, hold time, deflation time and rest time till the next cycle begins.

In a preferred embodiment, the treatment session further comprises the step of applying a dressing having a silver and/or honey anti-infection composition thereon to the ulcer area. The dressing advantageously has a sufficient amount of silver and/or honey to impede microbial growth in the ulcer area. The dressing preferably covers the ulcer and the PEMF applicator is placed on top of the dressing. In alternative embodiment, the method also includes the step of applying ultrasound to the ulcer area for a time sufficient to inhibit microbial growth.

In a preferred embodiment, the PEMF applications are each applied to the ulcer area for at least 10 minutes each and have the following functional settings: PEMF 1 has an applicator power output of 5 to 20 milli-Watts, a pulse rate (PR) of 60 to 100 pulses per second, and a pulse width (PW) of 55 to 70 microseconds; PEMF application 2 has an applicator power output of 15 to 35 milli-Watts, a PR of 300 to 600 pulses per second, and a PW of 45 to 70 microseconds; and PEMF application 3 has an applicator power output of 30 to 50 milli-Watts; a PR of 550 to 1050 pulses per second, and a PW of 35 to 70 microseconds.

A fourth PEMF application may also optionally be applied during the treatment session, PEMF application 4. PEMF application 4 preferably has an applicator power output of 30 to 50 milli-Watts; a PR of 3 to 8 pulses per second; and a PW of 2900 to 3300 microseconds.

In one exemplary embodiment, the PEMF application 1 has a PR of 80 pulses per second and a PW of 65 microseconds; the PEMF application 2 has a PR of 400 pulses per second and a PW of 65 microseconds; the PEMF application 3 has a PR of 600 pulses per second and a PW of 65 microseconds; and an optional PEMF application 4 has a PR of 5.6 pulses per second; and a PW of 3150 microseconds.

The PEMF applications can be administered in any order. For example, in one preferred embodiment, PEMF application 1 is applied first, followed by the PEMF application 3 and then the PEMF application 2. In yet another embodiment, the additional PEMF application 4 is applied between PEMF applications 3 and 2.

Additional PEMF applications can also be included per session as needed by the diabetic patient to properly heal the ulcer.

Advantageously, the PEMF application 1 preferably has a duty cycle of 0.30% to 0.70%, PEMF applications 2 a duty cycle of 1.4% to 4.2%, PEMF application 3 preferably has a duty cycle of 1.9% to 7.4%, PEMF application 4 preferably has a duty cycle of 0.3% to 2.6%. More preferably, PEMF application 1 has a duty cycle of 0.50%, PEMF application 2 has a duty cycle of 2.6%, PEMF application 3 has a duty cycle of 3.90%, and PEMF application 4 has a duty cycle of 1.8%.

In one embodiment, the ICT applications comprise at least one venous therapy, and at least one arterial therapy or venous/arterial therapy, each applied to the patient to increase blood flow and healing in the ulcer area. The venous therapy is designed to apply sufficient pressure to decrease venous congestion and increase the blood flow in the vein, which are closer to the surface of the skin, whereas the arterial therapy is designed to increase blood flow in the arteries, which are more deeply embedded in the patient and require greater pressure. The venous therapy preferably has an applied pressure range of between about 60 and 90 mmHg, whereas the arterial therapy preferably has an applied pressure range of between about 80 and 110 mmHg and the venous/arterial therapy having an applied pressure range of between 60 to 90 mmHg quickly followed by an applied pressure range of between 80 to 110 mmHg. The venous treatment is preferably applied between about 5 to 70 minutes per session and the arterial and/or arterial venous treatment is applied between about 100 to 200 minutes per session. In one preferred embodiment, the venous therapy is applied twice during the treatment session for between about 5 to 35 minutes each.

The ICT therapy can include intermittent, constant, gradated, sequential pressure, and continuous pressure therapy or any combination thereof. The venous therapy preferably has a pressure cycle of about 0.2 to 1.0 seconds to inflate, about 1.0 to 3.0 seconds of pressure holding, about 1.0 to 3.0 seconds deflating and about 10 to 20 seconds resting before the pressure cycle is repeated. The arterial therapy preferably has a pressure cycle of about 0.2 to 1.0 seconds to inflate, about 1.0 to 3.0 seconds pressure holding, about 1.0 to 3.0 seconds deflating and about 10 to 20 seconds resting before the pressure cycle is repeated. The venous/arterial therapy has a venous pressure cycle of about 0.2 to 1.0 seconds to inflate, about 0.2 to 1.0 seconds of pressure holding, about 0.1 to 3.0 seconds deflating; then while the venous pressure is deflating the arterial pressure is inflating for about 0.2 to 1.0 seconds, holding for about 1.0 to 3.0 seconds then deflating for about 1.0 to 3.0 seconds and resting for about 10 to 20 seconds before the venous/arterial pressure cycle is repeated.

In a preferred exemplary setting, the venous therapy pressure cycles is 0.5 seconds to inflate, 2 seconds holding the pressure, 2 seconds deflating and 15.5 seconds resting before the pressure cycle is repeated; the arterial therapy pressure cycle is 0.5 seconds to inflate, 2 seconds holding the pressure, 2 seconds deflating, and 15.5 seconds resting before the pressure cycle is repeated; and the venous/arterial pressure cycle has a venous pressure cycle of 0.5 seconds to inflate, 0.5 seconds of pressure holding, 0 to 2 seconds deflating; then while the venous pressure is deflating the arterial pressure is inflating for 0.5 seconds, holding the arterial pressure for 2.0 seconds then deflating for 2 seconds and resting for 14.5 seconds before the venous/arterial pressure cycle is repeated.

The duration of the venous therapy and the arterial therapy and/or the venous/arterial therapy preferably will differ according to the degree of ischemia to the ulcer area and patient sensitivity. The present method preferably has at least two settings for the ICT therapy to address moderate (a $TcPO_2$ of between 30-40 mmHG) and critical ischemia (a $TcPO_2$ of 30 mmHG or less). The ICT therapy to be administered is chosen based on the $TcPO_2$ of the ulcer area, such that, more time is spent during the therapy session applying the arterial or venous/arterial therapies the lower the $TcPO_2$. The preferred method also has at least two settings for the ICT therapy to address patient sensitivity, fragile and normal. The ICT sensitivity setting is set so that the greater the patient's sensitivity the lower the applied pressure used during the ICT therapy. In one preferred embodiment, the fragile setting is 10 mmHg lower than the normal setting. For example, the venous application ranges from 60 to 90 mmHg, with 80 mmHg being the setting for normal sensitivity and 70 being the typical setting for fragile sensitivity; likewise the arterial application range is from 80 to 110 mmHg, with 100 mmHg being the setting for normal sensitivity and 90 mmHg being the setting for fragile sensitivity. The patient sensitivity setting is preferably an objective decision made by the clinician and is based on a patient's total physiology and past skin condition, preferably including a number of variables including: age, past skin lesions/ulcers, past amputations, nutrition, weight, general health, etc.

DETAILED DESCRIPTION OF THE PREFERRED EMBODIMENTS

Figure 1:
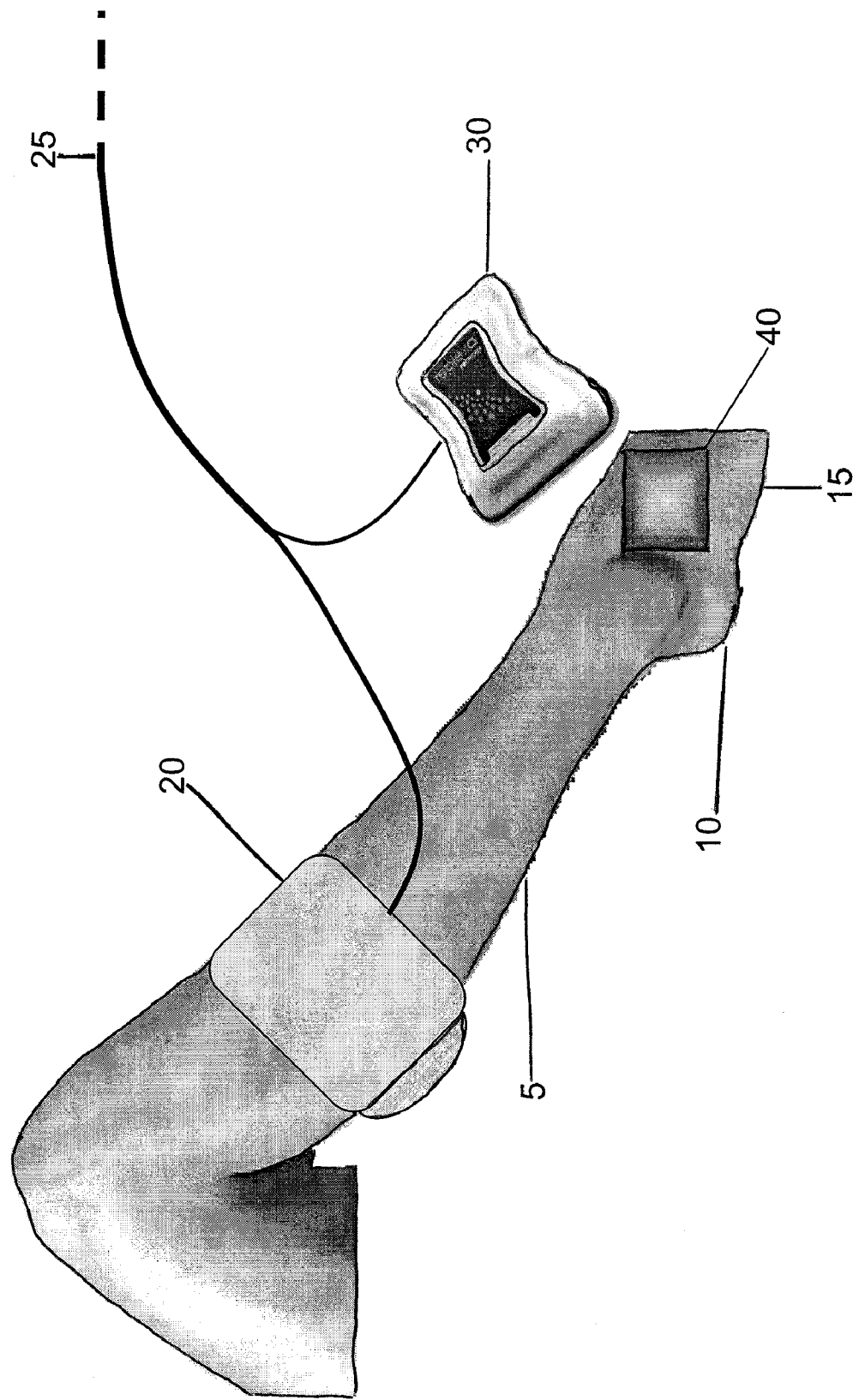
FIG. 1 shows a patient's lower extremity having a diabetic ulcer on the foot, a silver and/or honey dressing covering the ulcer area with the ICT applicator attached to the patient's leg above the diabetic ulcer and the PEMF applicator in preparation for administration of the treatment session. The PEMF applicator will be placed over the ulcer area when the treatment session beings.

The present invention is directed to methods of facilitating the healing of severe diabetic ulcers. A diabetic ulcer is a poorly healing ulcer, typically on one of the patient's extremities, such as a foot. Diabetic ulcers are typically caused by a combination of diabetes induced neuropathy and vascular disease. Severe diabetic ulcers are characterized by a diabetic wound that penetrates the subcutaneous fat layer, including those that penetrate the subcutaneous flat layer to the tendon, capsule, bone, or joint. Ischemia (moderate having a $TcPO_2$ of between 30-40 mmHg; critical ischemia having a $TcPO_2$ of 30 mmHg or less) and a slowdown in cell proliferation and wound healing are typical in diabetic ulcers. With this, infection is one of the many additional complications associated with severe diabetic ulcers that often lead to amputation in order to save the patient.

The term "patient" as used herein is directed to mammals, but preferably a patient is a human.

The term "about" as used herein, is intended to account for minor fluctuation due, for example those due to mechanical or human error that are within the spirit of the invention. The term "about" is preferably accounts for variation of less than 1% to 3%, and more preferably for variation of 1% or less.

As explained above, the present invention was developed specifically to treat severe diabetic ulcers, which if untreated could lead to multiple amputations of the patient's extremities. The present method comprises the steps of: administering to a diabetic patient, suffering from a severe diabetic ulcer a treatment session. The treatment session comprises at least three pulsed electromagnetic field (PEMF) applications, PEMF applications 1, 2, and 3, and at least two intermittent compression therapy (ICT) applications, typically including a venous, and an arterial therapy, a venous/arterial therapy, or combinations thereof. In a preferred embodiment, the ICT application includes a venous therapy and either an arterial therapy or venous/arterial therapy.

Referring to the drawing, FIG. 1 shows a patient's leg 5 and foot 15 having a diabetic ulcer 10 thereon. On top of the diabetic ulcer area 10 is placed a dressing 40 covering the ulcer area 10. The dressing 40 is impregnated with a silver and/or honey anti-infection composition in amounts sufficient to inhibit infection and microbial growth. An ICT applicator 20 and a PEMF Applicator 30 are connected to one or more cables 25 for connecting to the ICT compressor or PEMF energy generation device (not shown). The ICT applicator 20 is applied to the patient's leg 5 and the PEMF Applicator 30 is positioned near the ulcer area 10 and on top of the dressing in preparation of the treatment session. In one embodiment, not shown, the dressing 40 is part of the PEMF applicator 30 and the combined dressing/applicator 40/30 is placed directly on the diabetic ulcer area 10. A sock or other holder device (not shown) may be used to hold the PEMF Applicator 30 in place on the diabetic ulcer area 10 during the treatment session.

The treatment session preferably, is administered to the diabetic patient at least once a day to treat the severe diabetic ulcer, more preferably at least twice a day. Preferred treatment sessions are about 2.5 to 3.5 hours and are administered every 7 to 10 hours after completion of the previous treatment session.

The invention allows for delivery of specific types of both PEMF applications and ICT therapies at the same time or in close proximity during the treatment sessions to address the complex nature of severe diabetic ulcer to induce healing and preventing amputation. The PEMF and ICT applicator(s) can be used in conjunction with or without a wound dressing or cloth. The present invention will now be illustrated by the following non-limiting examples and description. In the following examples the devices have a generating device for generating PEMF energy or compression pressure that is connected to one or more separate applicators. The applicator(s) can apply the therapy to one or more areas of treatment. Preferably the applicator(s) are connected to the generating device by one or more cables/tubes. In an alternative embodiment, the generating device and applicator are combined into a single unit without the need for the cables/tubes.

PEMF Application: A PEMF applicator is preferably placed over the ulcer area. Direct contact of the PEMF application is not required, e.g., a dressing may be applied to the ulcer area and the applicator applied against the dressing. A PEMF applicator, or treatment pad, may consist of any suitable PEMF applicator known in the art, as long as the PEMF applicator can deliver the required PEMF application settings with the specific applicator power output, pulse rate and pulse width, as set forth herein. The PEMF application settings of the invention address specific factors that are necessary to induce healing of the diabetic ulcer. For example, PEMF application 1 is designed to induce cell activity necessary to prepare the ulcer bed for healing; PEMF application 2 induces cell activity necessary to fill in the ulcer bed near the surface of the patient's skin during the healing process or for shallower diabetic ulcers; PEMF application 3 is designed to induce cell activity to fill in the ulcer bed further from the surface. PEMF application 3 is especially important for deep problematic diabetic ulcers. An optional PEMF application 4 is designed to induce cell activity to fill in the wound bed for problematic diabetic ulcers that are not fully responsive to PEMF application 2 and/or 3.

ICT Therapy: The ICT therapy administered to the patient is chosen based on the level of ischemia and level of patient sensitivity. The ICT therapy preferably has at least two settings, a venous and arterial setting. The venous setting is used to address the patient's venous insufficiencies and the arterial setting is used to address the patient's arterial insufficiencies. In a preferred embodiment, a third optional ICT therapy setting, venous/arterial therapy, is used to address both the patient's venous and arterial insufficiencies in the ulcer area together at one time. In a preferred embodiment, the ICT therapies of the present invention are specifically designed to address the patient's vascular needs, having specific cycle of inflation time, hold time, deflation time and rest time till the next cycle begins.

The ICT therapies comprise the pressure applied; the type of pressure utilized (e.g. intermittent, constant, sequential, etc.), the amount of time to inflate (slow—rapid), the amount of time the pressure is held, the amount of time to release the pressure (deflate) and the rest period between pressure applications. In a preferred embodiment the ICT therapies comprise both a venous and an arterial therapy or optionally a venous/arterial therapy.

There are three main types of compression therapy, as set forth below:

Constant pressure therapy: Pressure is applied via an applicator in one spot or area of the patient's body, and the pressure remains at a fixed level for a specified time, and then pressure is taken off (released to ambient or "normal" pressure) for a specified time, and then pressure is reapplied at the fixed pressure level.

Gradated pressure therapy: Pressure is applied via an applicator in one spot or area of the patient's body, and the pressure initially is applied at a fixed level for a specified time, and then is immediately or gradually changed to a different (either higher or lower than the initial pressure) fixed pressure level, and then pressure is taken off (released to ambient or "normal" pressure) for a specified time, and then pressure is reapplied at initial fixed pressure level, and then immediately or gradually changed to the different fixed level. Although only two different pressure levels are discussed, it is possible to have more than two levels. For example, one could first apply pressure at 15 mmHg, then 30 mmHg, then 15 mmHg, then rest and repeat. Alternatively, one could apply pressure at 15, then 30, then 50 mmHg. Still further, the apparatus could apply pressure at 40, then 30, then 15, then 40 mmHg. Other combinations are possible as well and are envisioned by the present invention.

Sequential pressure therapy: Sequential pressure therapy requires that the device to permit pressure to be applied in at least two different spots or areas of the patient's body. This can be accomplished using a single applicator which has two or more chambers, each chamber capable of providing pressure at a different level (e.g., the first chamber provides 20 mmHg, the second provides 48 mmHg). Alternatively, this can be accomplished using two or more applicators, wherein each applicator provides pressure at a different level. (e.g., the first chamber provides 20 mmHg, the second provides 48 mmHg). In a preferred embodiment, the different applicators or different chambers used can act independently or in concert. Preferably the sequential pressure is applied in two areas that are in very close proximity but could include additional areas.

Variations and combinations of the three above types of therapy are also encompassed by the present invention. Examples of these variations and combinations include, for example:

Intermittent pressure therapy: Any of above three types of therapy start and stop at intervals for a set period of time.

In one non-limiting preferred embodiment, the venous therapy has a pressure cycle of about 0.2 to 1.0 seconds to inflate, about 1.0 to 3.0 seconds of pressure holding, about 1.0 to 3.0 seconds deflating and about 10 to 20 seconds resting before the pressure cycle is repeated; the arterial therapy has a pressure cycle of about 0.2 to 1.0 seconds to inflate, about 1.0 to 3.0 seconds pressure holding, about 1.0 to 3.0 seconds deflating and about 10 to 20 seconds resting before the pressure cycle is repeated; and the venous/arterial therapy has a venous pressure cycle of about 0.2 to 1.0 seconds to inflate, about 0.2 to 1 seconds of pressure holding, about 0.1 to 3.0 seconds deflating; then while the venous pressure is deflating the arterial pressure is inflating for about 0.2 to 1.0 seconds, holding for about 1.0 to 3.0 seconds then deflating for about 1.0 to 3.0 seconds and resting for about 10 to 20 seconds before the venous/arterial pressure cycle is repeated.

In a more preferred embodiment, the venous therapy pressure cycle is 0.5 seconds to inflate, 2 seconds holding the pressure, 2 seconds deflating and 15.5 seconds resting before the pressure cycle is repeated; the arterial therapy pressure cycle is 0.5 seconds to inflate, 2 seconds holding the pressure, 2 seconds deflating, and 15.5 seconds resting before the pressure cycle is repeated; and the venous/arterial pressure cycle has a venous pressure cycle of 0.5 seconds to inflate, 0.5 seconds of pressure holding, 0 to 2 seconds deflating; then while the venous pressure is deflating the arterial pressure is inflating for 0.5 seconds, holding the arterial pressure for 2.0 seconds then deflating for 2 seconds and resting for 14.5 seconds before the venous/arterial pressure cycle is repeated.

Silver and/or honey anti-infection dressing: In a preferred embodiment the method further comprises the step of applying to the ulcer area a dressing having a silver and/or honey anti-infection composition thereon in an amount sufficient to impede microbial growth in the ulcer area. The silver anti-infection composition can be any composition containing silver in sufficient quantities that it impedes microbial growth. In one non-limiting embodiment silver sol, described in U.S. Pat. No. 7,135,195 is used which is different than colloidal or ionic silver because it is permanently suspended in water where the mineral's charge is transferred to the entire body of water. Preferably, the silver sol is in a concentration of 10 to 45 ppm, more preferably, 15 to 40 ppm, 20 to 30 ppm, and most preferably about 32 ppm silver.

The honey anti-infection composition can also be any honey composition that impedes microbial growth. Preferably, however, the honey composition is Leptospermum (Manuka) honey that has an activity rating of 15+ or higher. In one non-limiting embodiment, the honey composition is as described in U.S. Pat. No. 6,956,144.

Ultrasound Therapy: Preferably the intensity used (power) for the ultrasound applicator is typically from 0.005-50.0 W/cm$^2$ and more preferably 0.01-5.0 W/cm$^2$ and most preferably 0.1-2.2 W/cm$^2$. In one particular preferred embodiment the ultrasound applicator provides a low frequency ultrasound between 01.5-0.3 W/cm$^2$. The frequency used is preferably 0.1-3000 kHz; more preferably 20-100 kHz; and most preferably 20-50 kHz. In certain embodiments wherein high frequency is implemented, the frequency may be from 1-10 MHz. Use of ultrasound application can vary from low to high frequency by first having low frequency; then switching to high frequency; then switching back to low; or any combination including always low or always high or whatever (e.g. L,L,H,L,H,L,H,H).

In addition, the treatment segment or the time that the applicator applies ultrasound before it stops can vary, examples include from 1 minute to constant (never stops until turned off). If a particular treatment segment is not constant then the total treatment can have multiple segments (each segment can have the same time or a different time).

In a non-limiting embodiment, the present invention also encompasses the use of a sensor to determine whether or not the applicator (or treatment pad) is accurately placed in contact with the portion of the patient's body to be treated. With respect to compliance monitoring, it is important to be able to make certain that a patient is actually using the device at all, and whether the patient is using it properly, particularly in situations, wherein the patient is provided with the device for use at the patient's home, wherein there is no medical personnel monitoring usage of the device around the clock.

The sensor may additionally or alternatively be provided with means to automatically turn off the device, should the sensor determine that the applicator is not being used, or is not being used accurately.

The applicator or sensor may additionally or alternatively be provided with an indicator means that is visible to the patient and/or clinician, which visually or aurally, and/or in another manner, advises the patient and/or clinician whether or not the applicator (or treatment pad) is accurately placed in contact with the portion of the patient's body to be treated. Examples of the indicator means are colored or white light emitting diodes (LED) and buzzers. As a specific example, a colored LED light turns on during the time when the device is being properly used. It is possible for the indicator means to be placed either on the applicator itself, or on the device, or in another suitable place, provided that it is visible or able to be heard by the patient and/or the clinician.

Examples of preferred embodiments of suitable treatment sessions include:

Example A: a treatment session wherein PEMF application 1 has an a pulse rate (PR) of 70 to 90 pulses per second, and a pulse width (PW) of 60 to 70 microseconds; the PEMF application 2 has a PR of 550 to 650 pulses per second, and a PW of 60 to 70 microseconds; and the PEMF application 3 has a PR of 550 to 650 pulses per second, and a PW of 60 to 70 microseconds; the venous therapy has an applied pressure range of between about 70 and 80 mmHg, and the arterial therapy having an applied pressure range of between about 90 and 100 mmHg, the treatment session being applied to the patient at least twice a day with at least 7 to 10 hours of rest between treatment sessions.

Example B: a treatment session comprising applying to the ulcer area a dressing having a silver and/or honey anti-infection composition thereon in an amount sufficient to impede microbial growth in the ulcer area; the PEMF application 1 has an applicator power output of 5 to 20 milli-Watts, a pulse rate (PR) of 60 to 100 pulses per second, and a pulse width (PW) of 55 to 70 microseconds; the PEMF application 2 has an applicator power output of 15 to 35 milli-Watts, a PR of 550 to 1050 pulses per second, and a PW of 45 to 70 microseconds; and the PEMF application 3 has an applicator power output of 30 to 50 milli-Watts; a PR of 550 to 1050 pulses per second, and a PW of 35 to 70 microseconds; the venous therapy has an applied pressure range of between about 60 and 90 mmHg, and the venous/arterial therapy having an applied pressure range of between 70 to 90 mmHg and an applied pressure range of between 90 to 110 mmHg, the treatment session being applied to the patient at least once a day to treat the severe diabetic ulcer.

Example C: a 3.5 hour treatment session twice a day with a 7 to 10 hour rest between treatments comprising, ICT Therapy for moderate or critical ischemia: 30 minutes of venous therapy (60 to 90 mmHg), 150 minutes of arterial therapy (80 to 110 mmHg) or venous/arterial therapy (70/90 or 80/110 mmHg) and 30 minutes of venous therapy; or 20 minutes of venous therapy, 170 minutes venous/arterial therapy and 20 minutes of venous therapy at the end of the treatment session; the venous therapy pressure cycle is 0.5 seconds to inflate, 2 seconds holding the pressure, 2 seconds deflating and 15.5 seconds resting before the pressure cycle is repeated; and the venous/arterial pressure cycle has a venous pressure cycle of 0.5 seconds to inflate, 0.5 seconds of pressure holding, 0 to 2 seconds deflating, then while the venous pressure is deflating the arterial pressure is inflating for 0.5 seconds, holding the arterial pressure for 2.0 seconds then deflating for 2 seconds and resting for 14.5 seconds before the venous/arterial pressure cycle is repeated; and PEMF Therapy: 20 minutes rest, 20 minutes of PEMF application 1 (PR 80, PW 65), 50 minutes rest, 30 minutes of PEMF application 3 (PR 600, PW 65), 50 minutes rest, 20 minutes of PEMF application 2 (PR 400, PW 65), and 20 minutes rest; or 20 minutes of PEMF application 1, 30 minutes rest, 40 minutes of PEMF application 3, 30 minutes rest, 40 minutes of PEMF application 4 (PR 5.6 and PW 3150), 30 minutes of rest, and 20 minutes of PEMF application 2.

EXAMPLES

A). PEMF Applications 1 and 3

Materials: Culture media (MEM) was obtained from Mediatech, Inc. (Herndon, Va.) for general culture of HEL (human embryonic lung fibroblasts). Fetal calf serum, penicillin/streptomycin, trypsin, 1×PBS, sodium pyruvate, and non-essential amino acids were purchased from VWR. Human embryonic lung fibroblast Cell Culture. Cells were obtained from Barrow Neurological Institute. Routine culture was performed as described (Ham and McKeehan, 1978). Briefly and as described below, cells were cultured in 10 cm plates at a density of 1.14×104 cells/cm2 in minimum essential media (MEM) supplemented with 1 mM sodium pyruvate, 1 mM non-essential amino acids, 100 units penicillin, 100 μg streptomycin, and 5% FCS. Cells were used for experimentation after 16 hours in a humidified incubator at 37° C. with 5% CO2. Cells were used for experimentation from passage 10-16.

Methods including PEMF conditions: Treatment was performed by exposing cells to PEMF at numerous settings to determine the best setting for fibroblast replication. We also applied a number of different assays to measure if other types of cell activity important to wound healing (e.g. neutrophil and macrophage attraction, protein, growth factor and cytikine interaction), were affected at different PEMF settings. Cells were plated in replicates of 10 at cell densities of 1×103, 5×103, and 1×104. The cells were allowed to grow for 12-14 hours and then exposed to the different PEMF treatments. Cells were treated for 30 minutes for any given condition (parameter) with a 2 inch (5.08 cm) saline bag placed between the treatment pad and the tissue culture plate. After treatment the cells were then grown for 12-16 hours after treatment. Quantitation of cell growth was measured using CyQUANT (Molecular Probes/Invitrogen) using the manufactures instructions. Cell growth was quantitated by reading the emission wavelength of 520 nm after excitation at 480 nm. A gain of 65 was used on the fluorescent plate reader.

The following is a step by step procedure,

Cell Proliferation Assay:

1.) Make up a concentrated cell suspension in growth media.

2.) Serial dilute the cell suspension so that in 100 μl either 1×103, 5×103 or 1×104 cells will be added to 10 independent wells for each cell density.

3.) Allow the cells to plate for 12-14 hours.

4.) Treat the cells with the parameters established.

5.) Allow the cells to grow after treatment for 12-14 hours.

6.) Wash the cells 2× with PBS and freeze at −80° C. for at least 1 hour.

7.) Add 100 μl of the CyQuant lysis/assay reagent and read at 520 nm emission/480 nm excitation.

Results: After comparing the wide variety of settings (e.g. variables included multiple settings in each of the following: Power, Pulse Rate, and Pulse Width); we found every setting showed some degree of improvement but one setting provided significantly better cell replication than the other settings. In the setting with an applicator Power Output of 15-25-35 mW, a Pulse Rate of 550-600-1050 pulses per second and a Pulse Width of 35-65-70 microseconds (PEMF application 3) provided a 24% improvement in cell replication—more than triple the cell replication of the other settings.

Further, a different setting with an applicator Power Output of 5-15-20 mW, a Pulse Rate of 60-80-100 pulses per second and a Pulse Width of 55-65-70 microseconds (PEMF application 1) had a greater positive impact on the other types of cell activity (e.g. neutrophil and macrophage attraction, protein, growth factor and cytikine interaction) than the other settings.

B). PEMF Application 3

Lab tests on PEMF parameters (applicator Power Output of 30-40-50 mW, a Pulse Rate of 550-600-1050 pulses per second and a Pulse Width of 35-65-70 microseconds) provide a more powerful field of energy further from the applicator surface. This more powerful setting allows the PEMF energy to penetrate into deeper wounds to enhance cell activity. Therefore, a more comprehensive treatment of deeper diabetic wounds is achieved. This becomes significant for wounds that are subcutaneous (e.g. wounds penetrating to the tendon, bone or joint) or where tunneling is observed.

3-D Mapping Lab Test Protocol: Field strength measurements were made using an Amplifier research Field Probe, Model FP4000. The field probe was used to measure and characterize the RF output field generated from a PEMF applicator. The first measurement was taken at the center of the applicator surface on top of a two inch 2% saline solution to mimic body mass. Subsequent surface measurements were made radially at increments of 2 cm also on top of the two inch 2% saline solution. The same procedure was repeated at distances of 2 cm, 4 cm, 6 cm and 8 cm from the surface of the applicator all through the two inch 2% saline solution. A total of 55 measurements for each setting (Power and Pulse Rate combination) tested were made. Results were recorded in Volts per meter (V/m).

Test Results: Test results indicate that higher PEMF energy output was achieved at all 55 data points when the optimal setting of applicator Power Output of 30-40-50 mW, a Pulse Rate of 550-600-1050 pulses per second and a Pulse Width of 35-65-70 microseconds was utilized. Measurements at the furthest point from the surface were up to 3 times that of other settings which leads to the conclusion that other settings may not provide sufficient energy to be effective in deep diabetic wounds.

The invention has been described in detail with particular reference to preferred embodiments thereof, but it will be understood by one of skill in the art that there are other variations and modifications that are within the spirit and scope of the invention. For example, it is understood that the PEMF treatment applications or ICT treatment applications can occur in varying orders during the treatment session, for example PEMF application 3, followed by PEMF application 1, PEMF application 4, and PEMF application 2. Therefore, it is intended that the invention encompass all changes and modifications that fall within the scope of the appended claims.

What is claimed is:

1. A method of treating a severe diabetic ulcer that penetrates the subcutaneous fat layer, the method comprising the steps of: administering a treatment session to a diabetic patient having a severe diabetic ulcer, the treatment session comprising at least three pulsed electromagnetic fields (PEMF) applications, PEMF applications 1, 2, and 3, and at least two intermittent compression therapy (ICT) applications, wherein the PEMF applications are each applied to the ulcer area for at least 10 minutes each and the PEMF application 1 has an applicator power output of 5 to 20 milli-Watts, a pulse rate (PR) of 60 to 100 pulses per second, and a pulse width (PW) of 55 to 70 microseconds; the PEMF application 2 has an applicator power output of 15 to 35 milli-Watts, a PR of 300 to 600 pulses per second, and a PW of 45 to 70 microseconds; and the PEMF application 3 has an applicator power output of 30 to 50 milli-Watts; a PR of 550 to 1050 pulses per second, and a PW of 35 to 70 microseconds; the ICT applications comprising at least one venous therapy and at least one arterial therapy or venous/arterial therapy each applied to the patient to increase blood flow and/or reduce vascular congestion to the severe diabetic ulcer area, wherein the venous therapy has an applied pressure range of between about 60 and 90 mmHg, the arterial therapy having an applied pressure range of between about 80 and 110 mmHg, and the venous/arterial therapy having an applied pressure range of between 60 to 90 mmHg followed by an applied pressure range of between 80 to 110 mmHg, the treatment session being applied to the patient at least once a day to treat the severe diabetic ulcer.

2. The method of claim 1, further comprising a fourth PEMF application, PEMF application 4, having an applicator power output of 30 to 50 milli-Watts; a PR of 3 to 8 pulses per second; and a PW of 2900 to 3300 microseconds.

3. The method of claim 2, wherein the PEMF application 1 has a PR of 80 pulses per second and a PW of 65 microseconds; the PEMF application 2 has a PR of 400 pulses per second and a PW of 65 microseconds; the PEMF application 3 has a PR of 600 pulses per second and a PW of 65 microseconds; and the PEMF application 4 has a PR of 5.6 pulses per second; and a PW of 3150 microseconds.

4. The method of claim 1, wherein the treatment session is at least about 2.5 to 3.5 hours.

5. The method of claim 4, wherein the treatment session is repeated every 7 to 10 hours after the previous treatment session has been completed.

6. The method of claim 1, wherein PEMF applications 1 and 2 are applied for between about 10 to 20 minutes each, the PEMF application 3 is applied for between about 20 to 40 minutes, and an optional PEMF application 4 being applied for between about 20 to 40 minutes.

7. The method of claim 1, wherein the PEMF application 1 is applied first, followed by the PEMF application 3 and then the PEMF application 2.

8. The method of claim 7, wherein a fourth PEMF application, PEMF application 4, is applied between PEMF applications 3 and 2.

9. The method of claim 1, further comprising the step of applying ultra-sound to the ulcer area.

10. The method of claim 1, further comprising the additional step of applying to the ulcer area a dressing having a silver and/or honey anti-infection composition thereon.

11. The method of claim 10, wherein the dressing covers the ulcer and the PEMF applicator is placed on top of the dressing.

12. The method of claim 1, wherein the PEMF application 1 has a duty cycle of 0.30% to 0.70% and PEMF applications 2 has a duty cycle of 1.4% to 4.2%, PEMF application 3 has a duty cycle of 1.9% to 7.4%, and an optional PEMF application 4 a duty cycle of 0.3% to 2.6%.

13. The method of claim 1, wherein the PEMF application 1 has a duty cycle of 0.50% and PEMF application 2 has a duty cycle of 2.6%; PEMF application 3 have a duty cycle of 3.90%; and an optional PEMF application 4 having a duty cycle of 1.8%.

14. The method of claim 1, wherein the patient is a human.

15. The method of claim 1, wherein the diabetic ulcer area is on one of the patient's extremities having a transcutaneous oxygen tension (TcPO2) of less than 40 mmHg.

16. The method of claim 15, wherein the extremity is severely ischemic having a $TcPO_2$ of 30 mmHg or less, and the extremity is the patient's foot.

17. The method of claim 15, wherein the pressure application of the arterial or venous/arterial therapy is adjusted based on the $TcPO_2$ for the ulcer area.

18. The method of claim 15, wherein ICT therapy setting is chosen based on the $TcPO_2$ of the patient's extremity, wherein more time is spent during the therapy session applying the arterial or venous/arterial therapies the lower the $TcPO_2$.

19. The method of claim 1, wherein the ICT therapy applied is based on the level of patient sensitivity relating to skin viability, wherein a lower the applied pressure is used for the ICT therapy for patients having greater sensitivity.

20. The method of claim 1, wherein the venous therapy is applied twice during the treatment session for between about 5 to 35 minutes per therapy and the arterial or arterial venous treatment is applied between about 100 to 200 minutes per session.

21. The method of claim 20, wherein the venous therapy has a pressure cycle of about 0.2 to 1.0 seconds to inflate, about 1.0 to 3.0 seconds of pressure holding, about 1.0 to 3.0 seconds deflating and about 10 to 20 seconds resting before the pressure cycle is repeated; the arterial therapy has a pressure cycle of about 0.2 to 1.0 seconds to inflate, about 1.0 to 3.0 seconds pressure holding, about 1.0 to 3.0 seconds deflating and about 10 to 20 seconds resting before the pressure cycle is repeated; and the venous/arterial therapy has a venous pressure cycle of about 0.2 to 1.0 seconds to inflate, about 0.2 to 1 seconds of pressure holding, about 0.1 to 3.0 seconds deflating; then while the venous pressure is deflating the arterial pressure is inflating for about 0.2 to 1.0 seconds, holding for about 1.0 to 3.0 seconds then deflating for about 1.0 to 3.0 seconds and resting for about 10 to 20 seconds before the venous/arterial pressure cycle is repeated.

22. The method of claim 21, wherein the venous therapy pressure cycle is 0.5 seconds to inflate, 2 seconds holding the pressure, 2 seconds deflating and 15.5 seconds resting before the pressure cycle is repeated; the arterial therapy pressure cycle is 0.5 seconds to inflate, 2 seconds holding the pressure, 2 seconds deflating, and 15.5 seconds resting before the pressure cycle is repeated; and the venous/arterial pressure cycle has a venous pressure cycle of 0.5 seconds to inflate, 0.5 seconds of pressure holding, 0 to 2 seconds deflating; then while the venous pressure is deflating the arterial pressure is inflating for 0.5 seconds, holding the arterial pressure for 2.0 seconds then deflating for 2 seconds and resting for 14.5 seconds before the venous/arterial pressure cycle is repeated.

23. The method of claim 1, wherein the severe diabetic ulcer penetrates the subcutaneous fat layer to the tendon, capsule, bone, or joint.

24. A method of treating a severe diabetic ulcer that penetrates the subcutaneous fat layer, the method comprising the steps of: administering a treatment session to a diabetic patient having a severe diabetic ulcer, the treatment session comprising at least three pulsed electromagnetic field (PEMF) applications, PEMF applications 1, 2, and 3, and at least two intermittent compression therapy (ICT) applications, wherein the PEMF applications are each applied to the ulcer area for at least 15 minutes each and the PEMF application 1 has an a pulse rate (PR) of 70 to 90 pulses per second, and a pulse width (PW) of 60 to 70 microseconds; the PEMF application 2 has a PR of 350 to 550 pulses per second, and a PW of 60 to 70 microseconds; and the PEMF application 3 has a PR of 550 to 650 pulses per second, and a PW of 60 to 70 microseconds; the ICT applications comprising at least one venous therapy and at least one arterial therapy or venous/arterial therapy each applied to the patient to increase blood flow to the severe diabetic ulcer area, wherein the venous therapy has an applied pressure range of between about 70 and 80 mmHg, the arterial therapy having an applied pressure range of between about 90 and 100 mmHg, and the venous/arterial therapy having an applied pressure range of between 70 to 80 mmHg and an applied pressure range of between 90 to 100 mmHg, the treatment session being applied to the patient at least twice a day with at least 7 to 10 hours of rest between treatment sessions to treat the severe diabetic ulcer.

25. A method of treating a severe diabetic ulcer that penetrates the subcutaneous fat layer, the method comprising the steps of: administering a treatment session to a diabetic patient having a severe diabetic ulcer, the treatment session comprising applying to the ulcer area a dressing having a silver and/or honey anti-infection composition thereon in an amount sufficient to impede microbial growth in the ulcer area, at least three pulsed electromagnetic field (PEMF) applications, PEMF applications 1, 2, and 3, and at least two intermittent compression therapy (ICT) applications, wherein the PEMF applications are each applied to the ulcer area for at least 10 minutes each and the PEMF application 1 has an applicator power output of 5 to 20 milli-Watts, a pulse rate (PR) of 60 to 100 pulses per second, and a pulse width (PW) of 55 to 70 microseconds; the PEMF application 2 has an applicator power output of 15 to 35 milli-Watts, a PR of 300 to 600 pulses per second, and a PW of 45 to 70 microseconds; and the PEMF application 3 has an applicator power output of 30 to 50 milli-Watts; a PR of 550 to 1050 pulses per second, and a PW of 35 to 70 microseconds; the ICT applications comprising at least one venous therapy and at least one arterial therapy or venous/arterial therapy each applied to the patient to increase blood flow to the severe diabetic ulcer area, wherein the venous therapy has an applied pressure range of between about 60 and 90 mmHg, the arterial therapy having an applied pressure range of between about 80 and 110 mmHg, and the venous/arterial therapy having an applied pressure range of between 60 to 90 mmHg followed by an applied pressure range of between 80 to 110 mmHg, the treatment session being applied to the patient at least once a day to treat the severe diabetic ulcer.

* * * * *